United States Patent [19]
Bass et al.

[11] Patent Number: 6,106,464
[45] Date of Patent: Aug. 22, 2000

[54] APPARATUS AND METHOD FOR BONE SURFACE-BASED REGISTRATION OF PHYSICAL SPACE WITH TOMOGRAPHIC IMAGES AND FOR GUIDING AN INSTRUMENT RELATIVE TO ANATOMICAL SITES IN THE IMAGE

[75] Inventors: Wayne A. Bass; Robert L. Galloway, Jr., both of Nashville, Tenn.; Calvin R. Maurer, Jr., Rochester; Robert J. Maciunas, Pittsford, both of N.Y.

[73] Assignee: Vanderbilt University, Nashville, Tenn.

[21] Appl. No.: 09/255,254

[22] Filed: Feb. 22, 1999

[51] Int. Cl.$^7$ ........................................ A61B 8/00
[52] U.S. Cl. ............................................. 600/439
[58] Field of Search ................... 600/407, 424, 600/437, 439, 443, 459, 471; 606/130

[56] References Cited

U.S. PATENT DOCUMENTS

| | | | |
|---|---|---|---|
| 5,394,875 | 3/1995 | Lewis et al. | 128/916 |
| 5,647,373 | 7/1997 | Polticli | 128/749 |
| 5,810,008 | 9/1998 | Debel et al. | 128/916 |
| 5,817,022 | 10/1998 | Vesely | 600/443 |
| 5,851,183 | 12/1998 | Bucholz | 600/425 |
| 5,957,844 | 9/1999 | Dehel et al. | 600/439 |

OTHER PUBLICATIONS

A. Gueziec and R. Hummel, "Exploiting Triangulated Surface Extraction Using Tetrahedral Decomposition," *IEEE Transactions On Visualization and Computer Graphics*, vol. 1, pp. 328–342, 1995.

P.J. Besl and M. D. McKay, "A Method For Registration Of 3D Shapes," *IEEE Trans PAMI*, vol. 14, pp. 239–256, 1992.

KB–Aerotech, "Ultrasonic Transducer Performance Parameters" "Effects on Diagnostic Imaging", *Aero–Tech Reports*, vol. 1, 4 pages, 1978.

T. Ault, M.W. Siegel, "Frameless Patient Registration Using Ultrasonic Imaging", *The Robotics Institute*, Carnegie Mellon University, pp. 1–9.

J.T. Lewis, R. L. Galloway, Jr., S. Schreiner, "An Ultrasonic Approach to Localization of Fiducial Markers for Interactive, Image–Guided Neurosurgery–Part I: Principles", *IEEE Transactions on Biomedical Engineering*, vol. 45, No. 5, pp. 620–630, May 1998.

S. Schrciner, R. L. Galloway, Jr., J.T. Lewis, W.A. Bass, D.M. Muratore, "An Ultrasonic Approach to Localization of Fiducial Markers for Interactive, Image–Guided Neurosurgery–Part II: Implementation and Automation", *IEEE Transactions on Biomedical Engineering*, vol. 45, No. 5, pp. 631–641, May 1998.

S. LaVallee, J. Troccaz, P. Sautot, B. Mazier, P. Cinquin, P. Merloz, J. Chirossel, "Computer–Assisted Spinal Surgery Using Anatomy–Based Registration", *Orthopaedics*, No. 32, pp. 425–449.

(List continued on next page.)

*Primary Examiner*—Francis J. Jaworski
*Attorney, Agent, or Firm*—Richard V. Westerhoff; Eckert Seamans Cherin & Mellott, LLC

[57] ABSTRACT

An A-mode ultrasound transducer is tracked in three-dimensions by an optical position tracking system as the transducer is scanned over the skin to generate measurements of bone surface distance from the transducer. A processor correlates the ultrasound data with position and orientation data to generate a three-dimensional physical space model of the bone surface which is registered with an image space model of the bone surface generated from a tomographic image to produce an alignment of the two models. The ultrasound transducer is replaced by an instrument which is also optically tracked. The alignment is used to translate instrument position in physical space to a position in image space for generation on a monitor of a composite display of the instrument and the tomographic image. This composite display can be used to guide positioning and orienting the instrument in physical space with respect to sites of interest observed in the tomographic image on the display.

23 Claims, 5 Drawing Sheets

OTHER PUBLICATIONS

R. Galloway, W.A. Bass, C.E. Hockey, "Task–oriented asymmetric multiprocessing for interactive image–guided surgery", Department of Biomedical Engineering and Department of Neurologic Surgery, Vanderbilt University; Northern Digital, Inc., Waterloo, Canada, Parallel Computing 24 (1998) 1323–1343, Jan. 15, 1998; revised Apr. 15, 1998.

P.A. Payne, "Medical and industrial applications of high resolution ultrasound", *J. Phys. E: Sci. Instrum*, vol. 18, 1985, pp. 465–473.

APPARATUS AND METHOD FOR BONE SURFACE-BASED REGISTRATION OF PHYSICAL SPACE WITH TOMOGRAPHIC IMAGES AND FOR GUIDING AN INSTRUMENT RELATIVE TO ANATOMICAL SITES IN THE IMAGE

BACKGROUND OF THE INVENTION

1. Field of the Invention

This invention relates to apparatus and a method for image-guided surgery or therapy. More particularly, it relates to apparatus which utilizes A-mode ultrasound to register physical space with a previously generated tomographic image to aid a surgeon in procedures such as brain surgery.

2. Background Information

In image-guided surgery, a previously generated tomographic image such as a computed tomography (CT) scan or a magnetic resonance image (MRI) is used to direct the surgeon to the site of interest. It is particularly useful in neurosurgery especially when a small entry through the skull is made or where the boundaries of the target tissue are not visible to the naked eye but are well delineated in the tomographic image. An important task in such a procedure is to define a relationship between the patient and the previously obtained images of the patient. In order to implement this task, a coordinate system is assigned to the physical space occupied by the patient. Since the images of a patient contain their own coordinate system, the task of relating the images to the patient can be accomplished by determining a mathematical relationship between the image coordinate system and the patient coordinate system. This mathematical relationship between coordinate systems is referred to as a registration and the two coordinate systems are said to be registered with respect to each other. When the two coordinate systems both arise from images of the patient, the registration is referred to as an image-space to image-space registration, or more simply an image-to-image registration. When one of the coordinate systems represents the actual patient, the registration is classified as an image space to physical space registration. Ideally, a point defined in one coordinate system will map to the identical point defined in the other coordinate system, but in reality, there is always some error associated with the relationship.

A known image-guided procedure is stereotactic surgery. In this technique, a large metal frame is secure by pins imbedded in the skull. An image such as a CT image of the head is then taken with the frame in place. A computer system is used to calculate settings on arcs on the frame for positioning instruments such as a biopsy probe to take a sample at a desired location in the brain. This is an invasive procedure which requires implantation of the pins in the skull. Images made before attachment of the pins in the frame are not useable. The stereotactic technique is not suitable for serial treatments as there are limitations on the duration that the pins can remain in place. Also, the pins project out of the skull and can be bent or misaligned. While the frame is also used to immobilize the patient's head, it is heavy and uncomfortable.

There have been efforts to eliminate the heavy frame required in stereotactic procedures. Most of the technologies involve registering skin surface in physical space and image space. Various systems have been proposed for establishing coordinates in physical space by tracking a probe as it is scanned over the skin surface. These include: articulated arm, active and passive optical, ultrasonic, electromagnetic and inertial systems. Such approaches have not resulted in very good accuracy however, mainly because the skin is deformable and thus establishing the precise position of the probe relative to undisturbed skin surface is difficult.

A different proposal suggests the implantation in the skull of fiducial markers which will appear in a subsequently taken tomographic image. An A-mode ultrasound transducer is then scanned over the skull to detect the position of the fiducial markers in physical or patient space. An optical tracking systems determines the position of the transducer in physical space. An algorithm is used to correlate the position of the probe in physical space to corresponding points on the skull in the image. Once this correlation has been made, the transducer can be replaced by a surgical probe which is also tracked by the optical tracking system. The position of the probe is projected onto the image to guide the surgeon in aligning entry through the skull. This procedure does not require any frame as in the stereotactic procedure. Furthermore, the fiducial markers can be flush with the surface of the skull. However, it is still an invasive procedure requiring implants in the skull.

A-mode ultrasound is used in dermatology, radiation oncology and even by farmers, all to measure skin thickness, but not to map bone surfaces.

There is a need for an improved non-invasive system and method for image-guided surgery and therapy.

In particular, there is a need for such a system and method which does not require implants in the skull.

There is an additional need for such a system and method which can utilize previously generated tomographic images thereby eliminating the need to take additional images at the time of surgery.

There is also a need for such a system and method which can be used for a sequence of treatments over an extended period of time.

There is a need for a system and method that meets all of these needs and yet is accurate and robust.

SUMMARY OF THE INVENTION

These needs and others are satisfied by the invention which is directed to apparatus and a method for bone surface-based registration of physical space with a tomographic image and for using this registration to guide positioning of a probe relative to the bone surface. It is based on the fact that bone, and particularly the skull, has surface irregularities and variations in curvature that can be localized using ultrasound. The irregularities and variations in curvature across the bone surface create local uniqueness that permits determination of the position of a probe over the bone surface. Detection of the precise location of a bone surface through covering layers of tissue is possible because ultrasound reflects at interfaces of regions with different acoustical impedances. The greater the difference in acoustical impedance the greater the reflection. The tissue-bone interface has a much greater reflection than the reflections at the interfaces between the different types of soft tissue covering the bone, such as dermis, subdermal layer, and subcutaneous fat. By registering the bone surface in image space derived from the tomographic image with the bone surface in physical space, more accurate correspondence between probe position and sites of interest in the tomographic image is established.

Apparatus in accordance with the invention includes an ultrasound transducer, and preferably an A-mode ultrasound transducer or an array of A-mode ultrasound transducers.

The transducer outputs ultrasound signals representative of the distance from the transducer to the bone surface as the probe is scanned over the bone surface. Position tracking means such as an optical tracking system generates position signals tracking the position and orientation of the transducer as the transducer is scanned over the bone surface. Means in the form of a trigger synchronize generation of the ultrasound signals with the position/orientation signals. An algorithm run by a processor such as a personal computer generates from the ultrasound signals and the position/orientation signals a three-dimensional physical space model of the bone surface. Another algorithm generates a three-dimensional image space model of the bone surface derived from the tomographic image. An alignment means generates an alignment of the physical space model and the image space model. This alignment is used by output means to generate an output. Preferably, this output means includes an instrument which replaces the ultrasound probe, a visual display, and means using the tracking signals tracking the position and orientation of the instrument and the alignment to generate on the visual display a composite image of the tomographic image and a representation of the instrument in image space.

Another aspect of the invention is apparatus for guiding the positioning of an instrument relative to a bone surface which is displayed in a tomographic image. Such apparatus includes the instrument and tracking means for tracking the instrument in physical space as it is moved over the bone surface. It further includes means providing an alignment of a model of the bone surface in physical space with a model of the bone surface in image space derived from the tomographic image. Means utilizing the tracking signals and the alignment generate on a visual display a composite image comprising a tomographic image and a representation of the instrument in image space.

The instrument can be any one of various passive or active devices used for treatment or diagnosis such as, for example, a surgical probe, a beam collimator emitting a beam, a cauterizer, a drill, a laser or a biopsy needle. The instrument can be positioned and oriented in physical space relative to sites of interest in the tomographic image by reference to the composite image on the display.

The invention also embraces a method of bone surface registration of physical space with a tomographic image. More specifically, it is directed to scanning an ultrasound transducer, and in particular an A-mode ultrasound transducer, or an array of A-mode ultrasound transducers over but spaced from the bone surface to generate ultrasound signals representing the distance between the transducer and the bone surface as the transducer is scanned over the bone surface. The position and orientation of the ultrasound transducer are tracked during scanning to generate transducer position/orientation signals. These tracking signals together with the ultrasound signals are used to generate a model of the bone surface in physical space. This physical space model is registered with an image space model derived from the tomographic image to produce an alignment of the two models. This alignment can be used to guide positioning and alignment of an instrument in physical space relative to selected sites in the tomographic image. The position and orientation of the instrument are tracked and used with the alignment to generate on a display a composite image including the tomographic image and a representation of the instrument in image space.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

The apparatus and method of the invention will be described as applied to surface-based registration of physical space with tomographic images using A-mode ultrasound for localization of the skull for image-guided neurosurgery and therapy. It will be appreciated that the invention can be used for generating and using physical space and image space model registration for other bone structures and for other procedures such as implanting screws and other prostheses.

Figure 1:
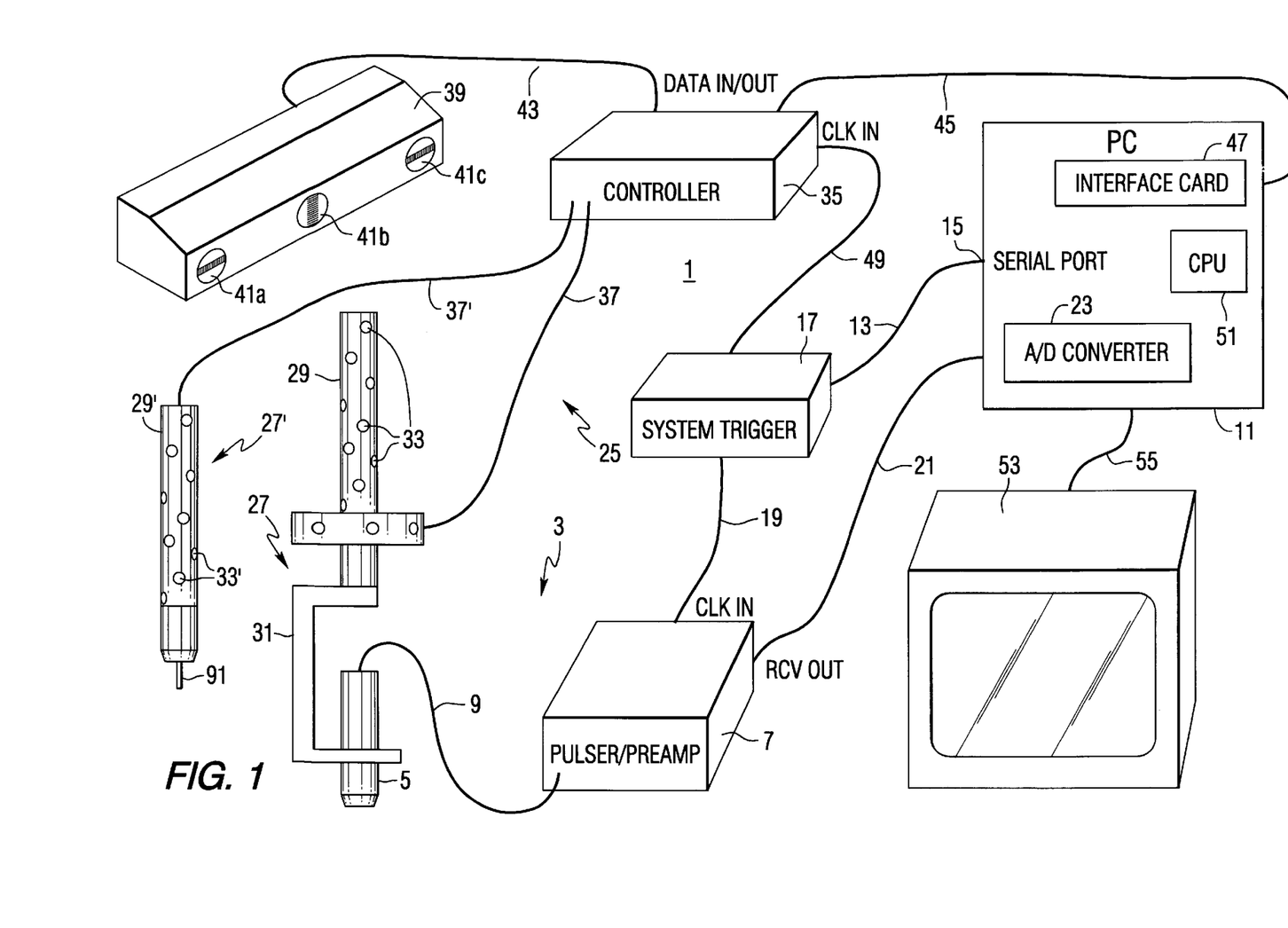
FIG. 1 is a schematic diagram of apparatus in accordance with the invention.

Turning to FIG. 1, the apparatus or system 1 of the invention includes an A-mode ultrasound subsystem 3 which utilizes an ultrasound transducer 5 and a pulser/preamplifier 7 connected by a cable 9. The pulser/preamplifier 7 generates electronic pulses which are converted to a narrow beam of ultrasound energy by the ultrasound transducer 5. Reflected energy from this beam is detected by the transducer 5 and converted to an electrical signal which is conditioned by the pulser preamplifier 7. A processor such as the personal computer 11 controls the ultrasound subsystem and also calculates the distance measurement between the ultrasound transducer 5 and the bone surface in a manner to be described. For control, the PC 11 provides a signal on lead 13 through the serial port 15 to a system trigger 17. The system trigger 17 triggers the pulser preamplifier 7 through lead 19 to initiate generation of the ultrasound pulse. The reflected signal received by the ultrasound transducer 5 and preprocessed by the preamplifier 7 is transmitted to the PC 11 over lead 21 where it is digitized by an analog to digital (A/D) converter 23 in the PC.

The position of the ultrasound transducer 5 is tracked by a position tracking system 25. The exemplary position tracking system 25 utilizes an optical tracking system such as the Optotrack® system manufactured by Northern Digital, Inc. This optical tracking system includes a tracking probe 27 made up of an elongated rigid body 29 and a special bracket 31 which mounts the ultrasound transducer 5 in axial alignment with the elongated body. Distributed over the elongated body are a number of infrared emitting diodes (IREDs) 33. A controller 35 sequentially turns on the IREDs through a cable 37. An optical receiver 39 has three charge coupled device (CCD) sensors 41a–c which translate light received from the IREDs into electrical signals which are passed to the controller 35 over the lead 43. The three sensors 41a–c are each mounted behind optical lenses that compress the two dimensional field of view into a one dimensional line focused on the CCDs. Each of the three sensors independently localizes the IRED to a spatial plane. The three sensor signals are used to compute the intersection of the three planes to establish the three-dimensional position and orientation of the ultrasound transducer 5, taking into account its offset on the probe. This position information is passed to the PC over lead 45 and input through interface card 47. The PC 11 also controls the position tracking system 25 through the system trigger 17 connected to the controller 35 by a cable 49. The exemplary tracking system is an active optical system. Other tracking systems including those referenced previously could be used. The active optical system is preferred because of its accuracy.

In order to gather data for generating a three-dimensional model of a bone surface, the PC 11 sends a command to the system trigger 17 which initiates generation of an ultrasound pulse by the ultrasound subsystem 3 while simultaneously initiating capture of the probe 27 position by the position tracking system 25. The trigger signals are generated at a rate of about 10 Hz. The optical tracking system sequences the IREDs and records positions at the rate of about 2500 Hz. The PC 11 includes a processor 51 which correlates the ultrasound data with the position tracking data and performs additional functions to be described to generate an output which is presented on an output device in the form of a visual display such as the monitor 53 connected to the PC by cable 55.

Figure 2:
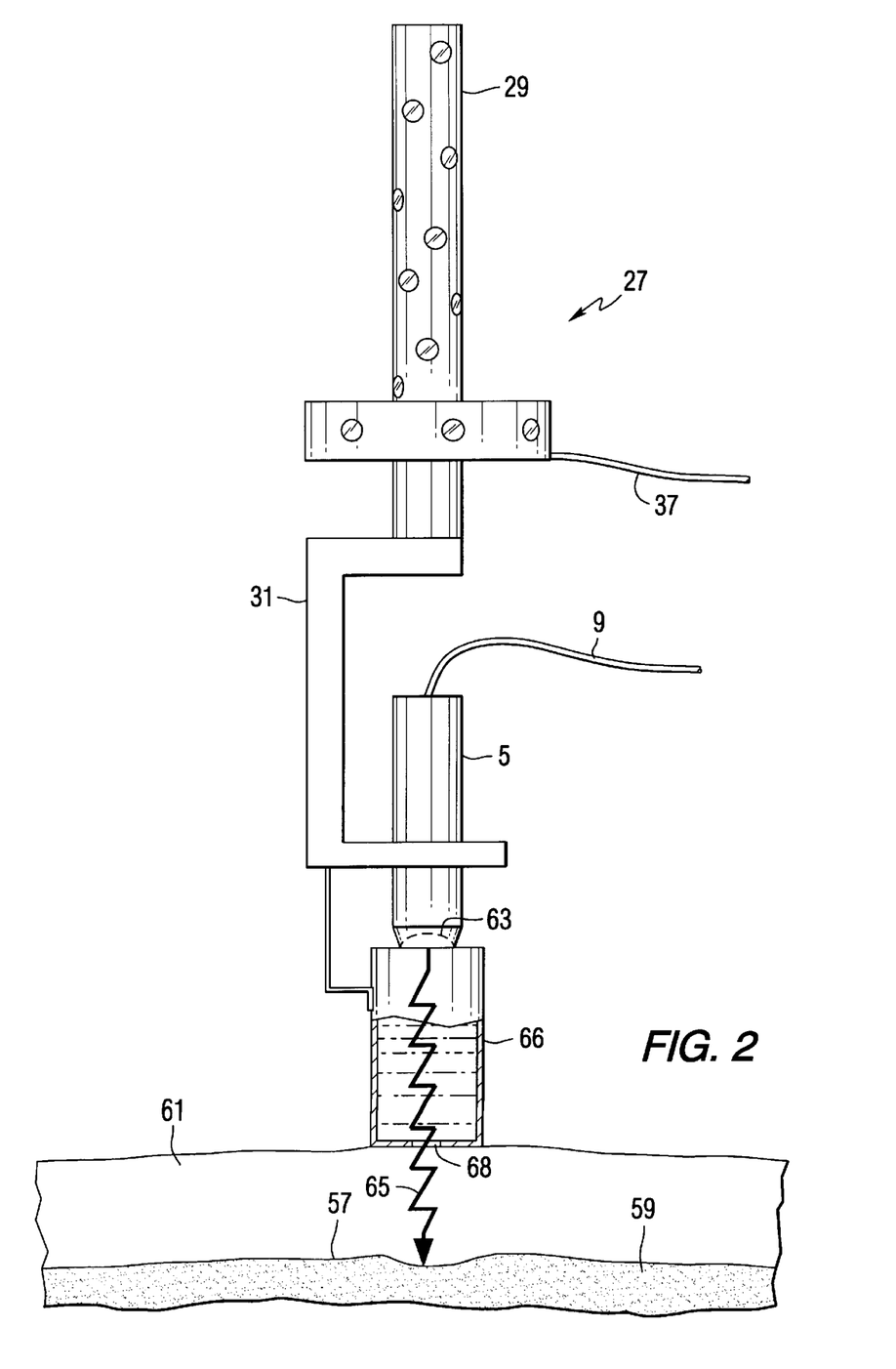
FIG. 2 is a schematic diagram illustrating operation of a part of the invention used to gather data for generating the three-dimensional model of a bone surface such as a skull in physical space.

FIG. 2 illustrates use of the system to map the surface 57 of a skull 59 which is covered by the scalp 61. The latter has been exaggerated for illustrative purposes as has the irregularity of the skull surface. The exemplary transducer 5 is a Panametrics 10.0 MHz emersion-type ultrasound transducer having a crystal 63 6.35 mm (0.25 inches) in diameter and spherically focused to a depth of 13.21 mm (0.52 inches) in water. The ultrasound pulse 65 emitted by the transducer 5 is reflected by the bone surface 57 for measuring the distance between the crystal 63 and the surface 57. As the ultrasound probe 27 is manually scanned over the scalp, the position tracking system sequences the IREDs 33 on the probe each time an ultrasound measurement is taken and calculates the position of the ultrasound transducer. As will be noticed, the bone surface 57 is not perfectly smooth so that variations in the measurements will be recorded. Even if there is variation in scalp thickness or distortion in thickness caused by pressure applied to the probe, the position tracking system takes into account these variables and the bone surface position in physical space is accurately determined. The ultrasound probe should be maintained substantially perpendicular to the bone surface for best results. With the probe maintained in this orientation as it is scanned, changes in curvature of the skull will be recorded in the data and aid in localization of the probe.

As mentioned, the preferred frequency of the ultrasound signal is 10 MHz. The selection of the frequency involves a tradeoff between increased axial resolution but also increased attenuation and thus decreasing return signal power with increasing frequency. Axial resolution in part is a function of the frequency of the transducer. At 10 MHz, axial resolution is about 0.15 mm, assuming a speed of sound in tissue of about 1,540 m/sec. Doubling the frequency would increase the resolution, but might make it more difficult to detect the signal peak. As a practical matter, the ultrasound frequency can be between about 5 and 20 MHz and preferably at about 10 MHz. There can also be variations in the speed of sound in tissue from the 1540 m/sec. just mentioned. For instance, a figure listed for fat is about 1480 m/sec. While most of the skin on the head is fat, it is thin, resulting in an error for a 5 mm skin thickness of 3% or about 0.15 mm.

The choice of crystal size and the use of a focused transducer are important. Good lateral resolution is desired, but not as critical as axial resolution. There are many tradeoffs among crystal size, focal distance, depth of focus and width. The crystal described above has a focal length of about 13 mm. As scalp thickness is typically about 4–6 mm, a water offset of about 7–9 mm such as provided by the water cylinder 66 is interposed between the crystal and the scalp so that the beam is focused on the bone surface. Alternatively, a water bag of similar thickness could be laid over the scalp. This eliminates the need for an ultrasound coupling gel that would otherwise need to be applied to the scalp to reduce the acoustic impedance problem associated with an air-skin interface. It introduces a problem of reflections at the water plastic interface, but this can be overcome by cutting a hole 68 in the plastic sufficiently small, e.g. about 6 mm, that surface tension keeps the water in the offset and the water couples directly to the skin. Where the transducer has a focal length such that the scalp thickness falls within the focal depth, the offset is not needed, but coupling gel should be used to eliminate the air scalp interface.

A-mode ultrasound utilizes a single narrow beam of ultrasound energy which is scanned over the scalp. Acquisition of ultrasound data can be expedited by using an array of such A-mode ultrasound transducers.

Figure 3:
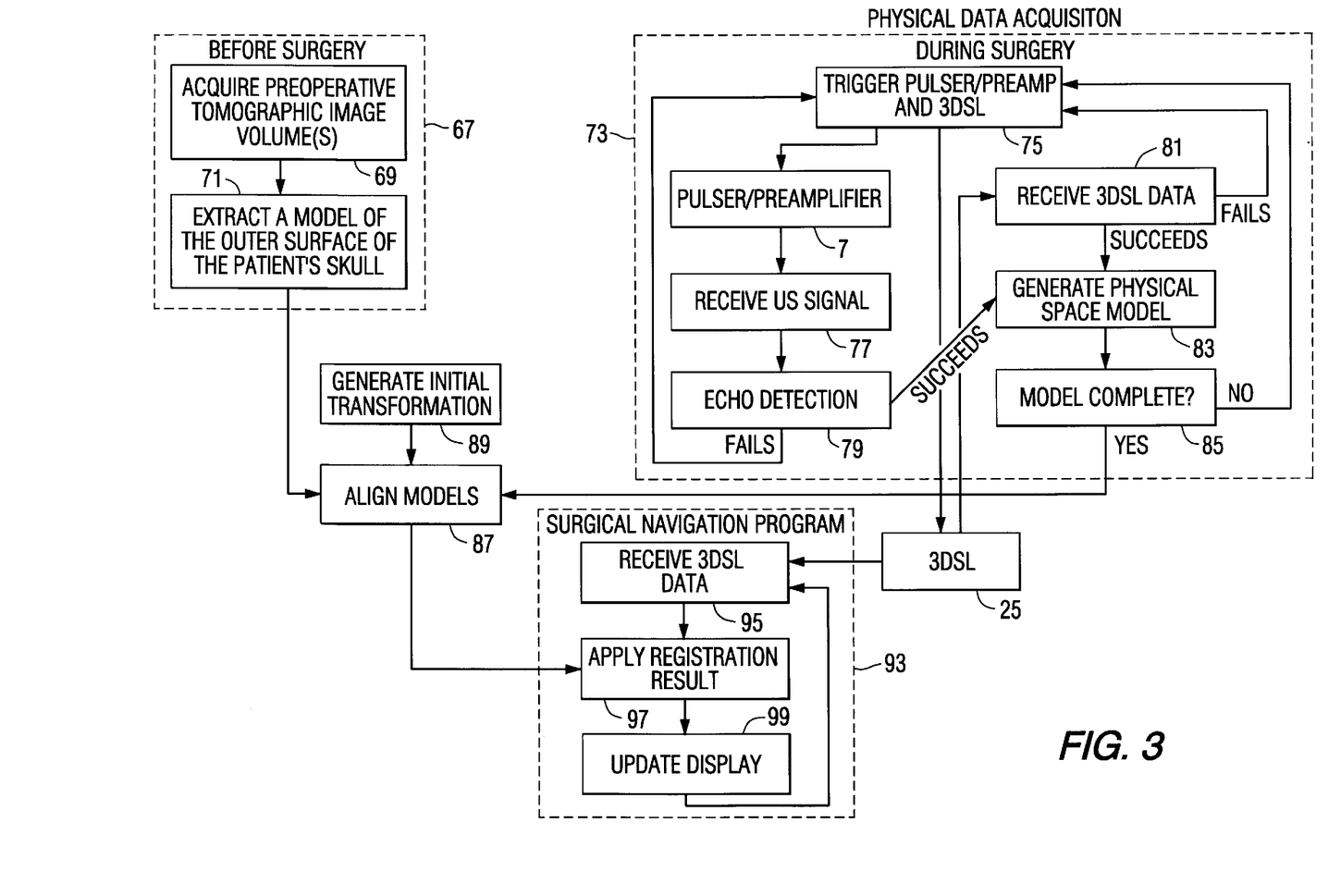
FIG. 3 is a functional diagram of the invention in block form.

FIG. 3 is a functional diagram of the invention. As indicated in the upper left, before surgery 67, preoperative tomographic image volumes are acquired at 69. This can be, for instance, a computed tomography (CT) image, a magnetic resonance imaging (MRI) image or a position emission tomography (PET) image, as is well known. A three-dimensional model of the outer surface of the bone, such as the skull, is then extracted at 71. Such procedures are known. See A. Gueziec and R. Hummel, "Exploiting Triangulated Surface Extraction Using Tetrahedral Decomposition," *IEEE Transactions On Visualization and Computer Graphics*, Vol. 1, pp. 328–342, 1995, and G. Aboutanos, "Image-Based Deformable Models For 3-D Automatic Segmentation Of The Brain," Ph.D. Dissertation, *Department of Electrical Engineering*, Vanderbilt University, Nashville, Tenn. 1996.

During surgery, physical data acquisition 73 includes triggering of the pulser preamplifier 7 and the three-dimensional surface localization (3DSL), or position tracking system, at 75. As mentioned, this simultaneously initiates generation of an ultrasound pulse and measurement of probe position. The PC 11 then receives the ultrasound signal at 77 and detects the echo in a manner to be described in connection with FIG. 5. The PC also receives the position data at 81. If for some reason valid 3D data or a valid echo is not detected, the data is ignored. If a valid echo and reliable position data for that echo are received, then the data is combined at 83 for generation of the model of the bone surface in physical space. In this process the time of flight of the ultrasound pulse is used to calculate the spacing between the ultrasound transducer and the bone surface and this offset is used with the 3D data to determine the position of the sample point on the bone surface in physical space. This process is continued at 85 until the model of the bone surface in physical space is completed. It is not necessary to generate a model of the entire bone surface such as is done with the image space model. The bone surface points generated from the position/orientation data and the corresponding ultrasound measurements of the distance from the transducer to the bone surface are registered on the bone surface modeled from the tomographic image. Hence, as used herein, references to the physical space model include that provided by the calculated bone surface points in physical space, which could be developed into continuous function representing the bone surface in physical space.

Next, an alignment of the image-based model derived from the tomographic image at 71, and the physical space model generated from the ultrasound subsystem and the position tracking system generated at 83 and 85 is implemented at 87. A suitable method for bringing the two models into registration is described in P. J. Besl and M. D. McKay, "A Method For Registration Of 3D Shapes," *IEEE Trans PAMI*, Vol. 14, pp. 239–256, 1992. A faster version of this algorithm is found in D. A. Simon, "Fast And Accurate Shape-Based Registration," *Robotics*, Pittsburgh, Pa.: Carnegie Mellon University, 1996, pp. 196. In order to reduce the time required to produce the alignment of the models, an initial transformation is generated at 89. As is known, the initial transformation produces a rough alignment. It is an interactive process in which a small number of anatomic points are initially identified in the two models. While an alignment can be produced without the initial transformation, the time required for registration of the images to produce the alignment is greatly reduced through use of the initial transformation.

With the alignment of the models completed, the system is ready for use in image-guided surgery. Returning to FIG. 1 for a moment, as the ultrasound transducer 5 is no longer needed, the probe 27 can be replaced with a probe 27' which attaches an instrument 91 such as a surgical probe or other passive pointing device secured to the elongated body 29' having IREDs 33' sequentially energized by the controller 35 through the lead 37'. The optical tracking system will then track the instantaneous position and orientation of the probe 91 as it is moved over the scalp. As ultrasound measurements are not being generated at this point, the frequency of the optical measurements can be increased to increase the responsiveness of the tracking of the probe 91. For instance, the frequency of the optical tracking system can be increased from 10 Hz to about 40 Hz or more.

Figure 4:
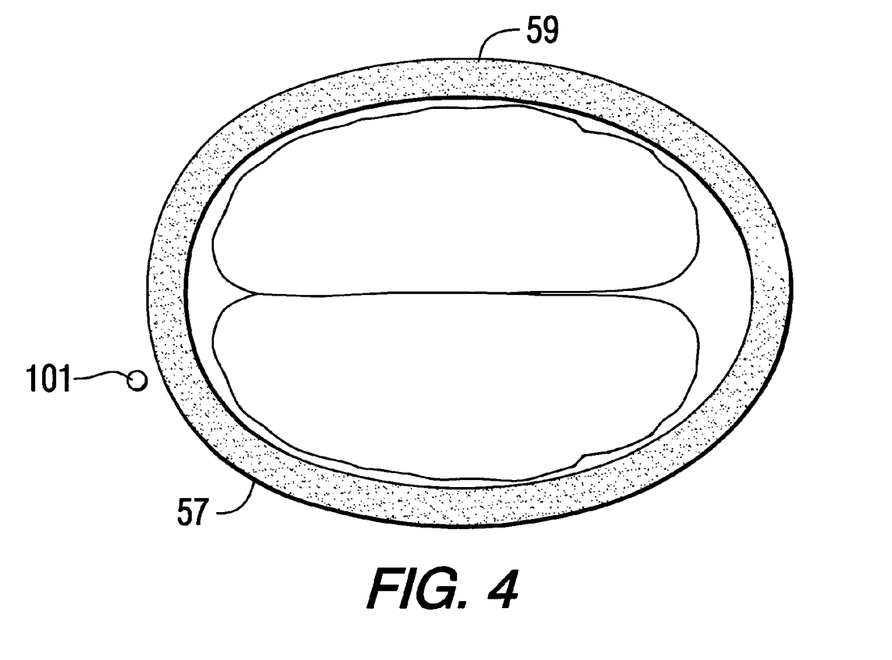
FIG. 4 illustrates a display generated by the invention which can be used in image-guided surgery or therapy.

Returning to FIG. 3, surgical navigation programs 93 are available for using the model alignment and the signals supplied by the optical tracking system 25 to track the position of the surgical probe 91 as it is moved over the skull. For instance, see R. L. Galloway, et al., "Task-Oriented Asymmetric Multi-Processing For Interactive Image-Guided Surgery," *Parallel Computing*, Vol. 24, pp. 1323–1343, 1998. This surgical navigation program 93 receives the position data from the position tracking system at 95 and applies at 97 the registration data from the alignment 87 to generate a representation of the position of the probe in the tomographic image which is displayed on the monitor 53 at 99. FIG. 4 shows an example of a composite image generated by the invention. In the simplified example, the position of the probe 91 is indicated by the dot 101 on the tomographic image. As is known, a realistic image of the probe can be projected onto the tomographic image in place of the representative dot shown.

Figure 5:
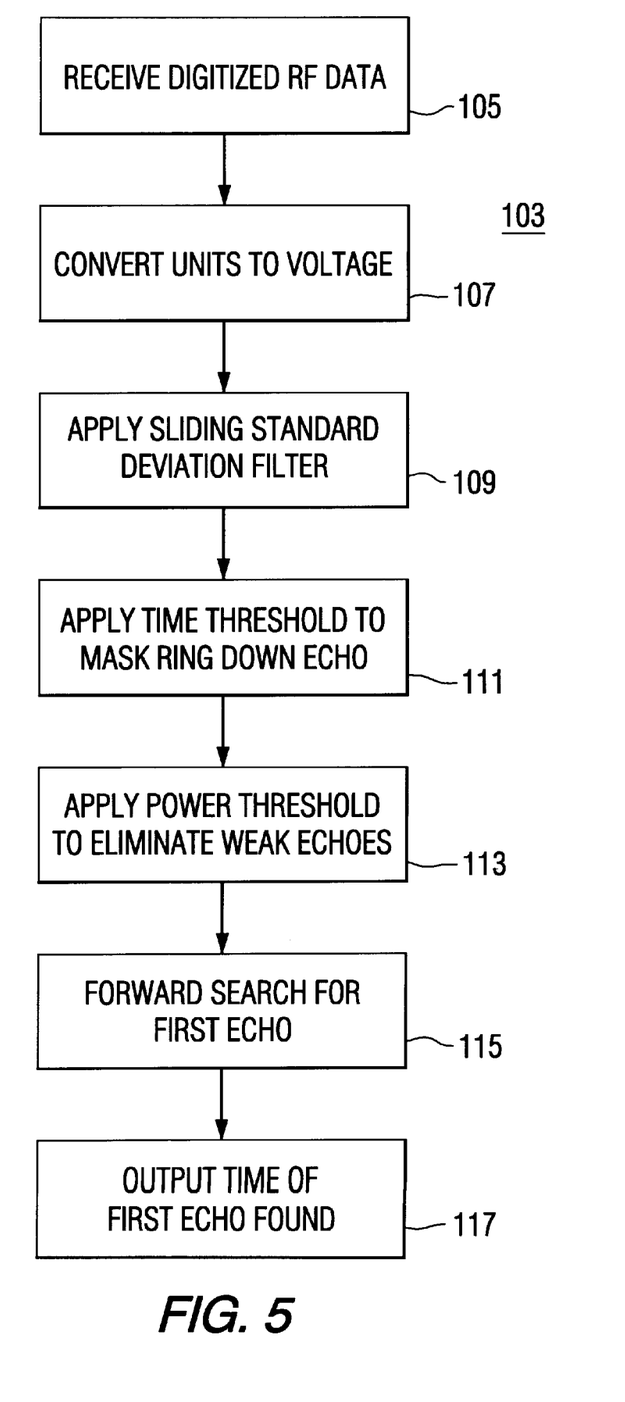
FIG. 5 is a flow chart of a software program for extracting echoes representing the distance of the bone surface from the transducer.

FIG. 5 is a flow chart 103 of the echo detection algorithm used by the PC 11 to determine the exact point in the ultrasound signal representing the reflection from the bone surface. The digitized data from the ultrasound subsystem is received at 105 and converted to voltage units at 107. A standard deviation filter is applied at 109 to assist in locating echoes within the ultrasound signals. A time threshold is applied at 111 to eliminate ring-down produced by the crystal 63 following generation of the pulse. In addition, a power threshold is applied at 113 to eliminate weak echoes which could be produced, for instance, by boundaries between skin, muscle and fat in the scalp. A forward search is then made for the first echo at 115 which will be the very large response that should be received from the bone surface. The difference between the time that the ultrasound pulse is launched and the time that this first echo is received is then out-put at 117 for use in computing the distance from the probe to the bone surface using the conventional time of flight calculation.

An alternative technique for signal detection utilizes the Hilbert transform which is used in communications to find signal envelopes. This method includes the steps of: 1) band-pass the signal (e.g., between 2 and 20 MHz). 2) Calculate the Hilbert transform of the signal. Denote the signal by x(t) and the Hilbert transform of the signal by H(t). The Hilbert transform can be calculated in the time or the frequency domain. 3) Calculate the complex analytical signal q(t)=x(t)+i h(t). The i is the imaginary i such that i^2=−1. 4) Calculate the magnitude of the analytical signal. This represents the envelope of the ultrasound signal, and there will be a peak at each interface with a very large peak at the tissue-bone interface.

With the present invention, no fiducial markers need to be imbedded in the bone. Hence, previously generated tomographic images can be used and there is no restriction on using the system repetitively for serial procedures, as is the case where fiducial markers having a limitation on the time they can remain in place are used. The need for the cumbersome stereotactic frame is also eliminated by the described apparatus for registering physical space with image space and for guiding a surgical probe.

Various instruments 91 can be positioned and oriented using the invention. For instance, in addition to the surgical probe, a beam collimator emitting a beam such as an x-ray beam can be guided to deliver a dose of radiation to a location in the brain identified from the tomographic image. In addition, cauterizers, drills, lasers and biopsy needles can be guided by reference to the composite image.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. Apparatus for bone surface-based registration of physical space with a tomographic image, comprising:

an ultrasound transducer generating ultrasound signals representative of a distance from said transducer to said bone surface as said transducer is scanned over but spaced from said bone surface;

tracking means generating transducer position/orientation signals tracking transducer position and orientation as said transducer is scanned over said bone surface;

means synchronizing generation of said ultrasound signals with generation of said position signals;

physical model generating means generating from said ultrasound signals and transducer position/orientation signals a three-dimensional physical space model of said bone surface;

means generating a three-dimensional image space model of said bone surface from said tomographic image;

means generating an alignment of said physical space model and said image space model; and output means generating an output utilizing said alignment.

2. The apparatus of claim 1 wherein said ultrasound transducer comprises an A-mode ultrasound transducer.

3. The apparatus of claim 2 wherein said output means comprises an instrument tracked by said tracking means to generate instrument position/orientation signals, a visual display, and means using said instrument position/orientation signals and said alignment for generating on said visual display a composite image comprising said tomographic image and a representation of said instrument in image space.

4. The apparatus of claim 3 wherein said tracking means comprises optical tracking means.

5. The apparatus of claim 3 wherein said instrument is selected from a group consisting of: a surgical probe, a beam collimator emitting a beam, a cauterizer, a laser, a drill and a biopsy needle.

6. The apparatus of claim 5 wherein said ultrasound transducer comprises an A-mode ultrasound transducer.

7. The apparatus of claim 6 wherein said tracking means comprises optical tracking means.

8. The apparatus of claim 3 wherein said A-mode ultrasound transducer operates at about 5–20 MHz.

9. The apparatus of claim 8 wherein said A-mode ultrasound transducer operates at about 10 MHz.

10. The apparatus of claim 2 wherein said tracking means comprises optical tracking means.

11. The apparatus of claim 2 wherein said ultrasound transducer comprises an array of ultrasound transducers.

12. The apparatus of claim 2 wherein said A-mode ultrasound transducer has a predetermined focal length and including an offset which spaces said transducer from said bone surface by about said focal length.

13. The apparatus of claim 12 wherein said offset contains water.

14. The apparatus of claim 13 wherein said offset is a container containing water and having an end wall facing toward said bone surface having an aperture through which said ultrasound transducer is focused and being of size that water surface tension maintains said water in said container.

15. Apparatus for guiding positioning of an instrument relative to a bone surface displayed in a tomographic image, said apparatus comprising:

an instrument;

tracking means generating tracking signals tracking position and orientation of said instrument in physical space;

means providing an alignment of a model of said bone surface in physical space with a model of said bone surface in image space with the latter derived from said tomographic image;

a visual display; and means using said tracking signals and said alignment to generate on said visual display a composite image comprising said tomographic image and a representation of said instrument in image space.

16. The apparatus of claim 15 wherein said tracking means is optical tracking means.

17. The apparatus of claim 16 wherein said instrument is selected from a group consisting of: a surgical probe, a beam collimator emitting a beam, a cauterizer, a laser, a drill and a biopsy needle.

18. The apparatus of claim 16 wherein said means providing said alignment includes A-mode ultrasound means for generating said model of said bone surface in physical space.

19. A method of bone surface-based registration of physical space with a tomographic image comprising the steps of:

scanning an ultrasound transducer over but spaced from a bone surface to generate ultrasound signals representing a distance between the transducer and the bone surface;

tracking the transducer position and orientation as the transducer is scanned over said bone surface to generate transducer position/orientation signals;

generating a physical space model of said bone surface from said ultrasound signals and said transducer position/orientation signals;

generating an image space model from said tomographic image; and registering the physical space model with the image space model to produce an alignment of said physical space model and said image space model.

20. The method of claim 19 further including tracking an instrument relative to said bone surface to generate instrument position/orientation signals; using said alignment and said instrument position/orientation signals to generate a representation of said instrument in image space; and generating on a display a composite image of said representation of said instrument in image space and said tomographic image, and using said display to position and orient said instrument in physical space.

21. The method of claim 20 wherein said instrument is selected from a group consisting of: a surgical probe, a beam collimator emitting a beam, a cauterizer, a laser, a drill and a biopsy needle.

22. The method of claim 19 wherein said ultrasound transducer is an A-mode ultrasound transducer.

23. The method of claim 19 wherein said ultrasound transducer is an array of A-mode ultrasound transducers.

* * * * *